(12) United States Patent
Takayama et al.

(10) Patent No.: US 7,704,728 B2
(45) Date of Patent: Apr. 27, 2010

(54) MICROFLUIDIC GRAVITY PUMP WITH CONSTANT FLOW RATE

(75) Inventors: Shuichi Takayama, Ann Arbor, MI (US); Joseph Chang, Ann Arbor, MI (US); Dongeun Huh, Stanford, CA (US); Xiaoyue Zhu, Ann Arbor, MI (US); Brenda Cho, Ann Arbor, MI (US); Gary D. Smith, Ann Arbor, MI (US)

(73) Assignee: The University of Michigan, Ann Arbor, MI (US)

( * ) Notice: Subject to any disclaimer, the term of this patent is extended or adjusted under 35 U.S.C. 154(b) by 1004 days.

(21) Appl. No.: 10/198,477

(22) Filed: Jul. 18, 2002

(65) Prior Publication Data
US 2003/0096405 A1 May 22, 2003

Related U.S. Application Data

(60) Provisional application No. 60/306,292, filed on Jul. 18, 2001.

(51) Int. Cl.
*C12M 1/36* (2006.01)

(52) U.S. Cl. .................... 435/286.5; 435/286.4; 436/52; 137/1; 137/8; 137/246.23

(58) Field of Classification Search .................. 435/6, 435/325; 436/172, 518; 422/52, 61; 137/1
See application file for complete search history.

(56) References Cited

U.S. PATENT DOCUMENTS

| 6,066,448 | A  | * | 5/2000  | Wohlstadter et al. ........... 435/6 |
| 6,349,740 | B1 | * | 2/2002  | Cho et al. ................. 137/487.5 |
| 6,491,666 | B1 | * | 12/2002 | Santini et al. ................ 604/191 |
| 6,499,499 | B2 | * | 12/2002 | Dantsker et al. ................ 137/1 |
| 2001/0027745 | A1 | * | 10/2001 | Weigl et al. .................. 117/206 |
| 2001/0036626 | A1 | * | 11/2001 | Farinas et al. ................... 435/4 |
| 2001/0048088 | A1 | * | 12/2001 | Polla et al. ............. 251/129.06 |
| 2002/0016019 | A1 | * | 2/2002  | Ikeno .......................... 438/106 |
| 2002/0017484 | A1 | * | 2/2002  | Dourdeville ............. 210/198.2 |
| 2002/0086340 | A1 | * | 7/2002  | Veerapandian et al. ..... 435/7.23 |
| 2003/0040119 | A1 | * | 2/2003  | Takayama et al. ............. 436/63 |
| 2003/0190608 | A1 | * | 10/2003 | Blackburn ..................... 435/6 |

FOREIGN PATENT DOCUMENTS

WO      WO 01/26813 A2    4/2001

OTHER PUBLICATIONS

B. Cho et al., "Proceedings of the IEEE-EMBS Conference on Microtechnologies in Medicine and Biology," pp. 156-159, (2002).

(Continued)

*Primary Examiner*—Nelson Yang
(74) *Attorney, Agent, or Firm*—Brooks Kushman P.C.

(57) ABSTRACT

A microfluidic system employs a microchannel and a gravity driven pump comprising horizontally oriented fluid supply reservoirs which supplies fluid to the microchannel at a substantially constant rate. The device is useful for numerous microfluidic applications, for example in the culture and/or treatment of biological systems under constant flow-induced stress, cell-size sorting, motile sperm sorting, or embryo culture.

21 Claims, 3 Drawing Sheets

OTHER PUBLICATIONS

D. Huh et al., Proceedings of the 2nd IEEG-EMBS Conference, pp. 466-469 (2002).

S. Nonaka et al., "Determination of Left-Right Patterning of the Mouse Embryo by Artificial Nodal Flow," Nature, 418, pp. 96-99, Jul. 2002.

S. Takayama et al., "Patterning Cells and Their Environment Using Multiple Laminar Fluid Flows in Capillary Networks," Proc. Natl. Acad. Sci. USA, pp. 5545-5548, 1999.

Duffy et al., Rapid Prototyping of Microfluidic Systems in Poly(dimethylsiloxane), Anal. Chem., 70, pp. 4974-4984, 1998.

* cited by examiner

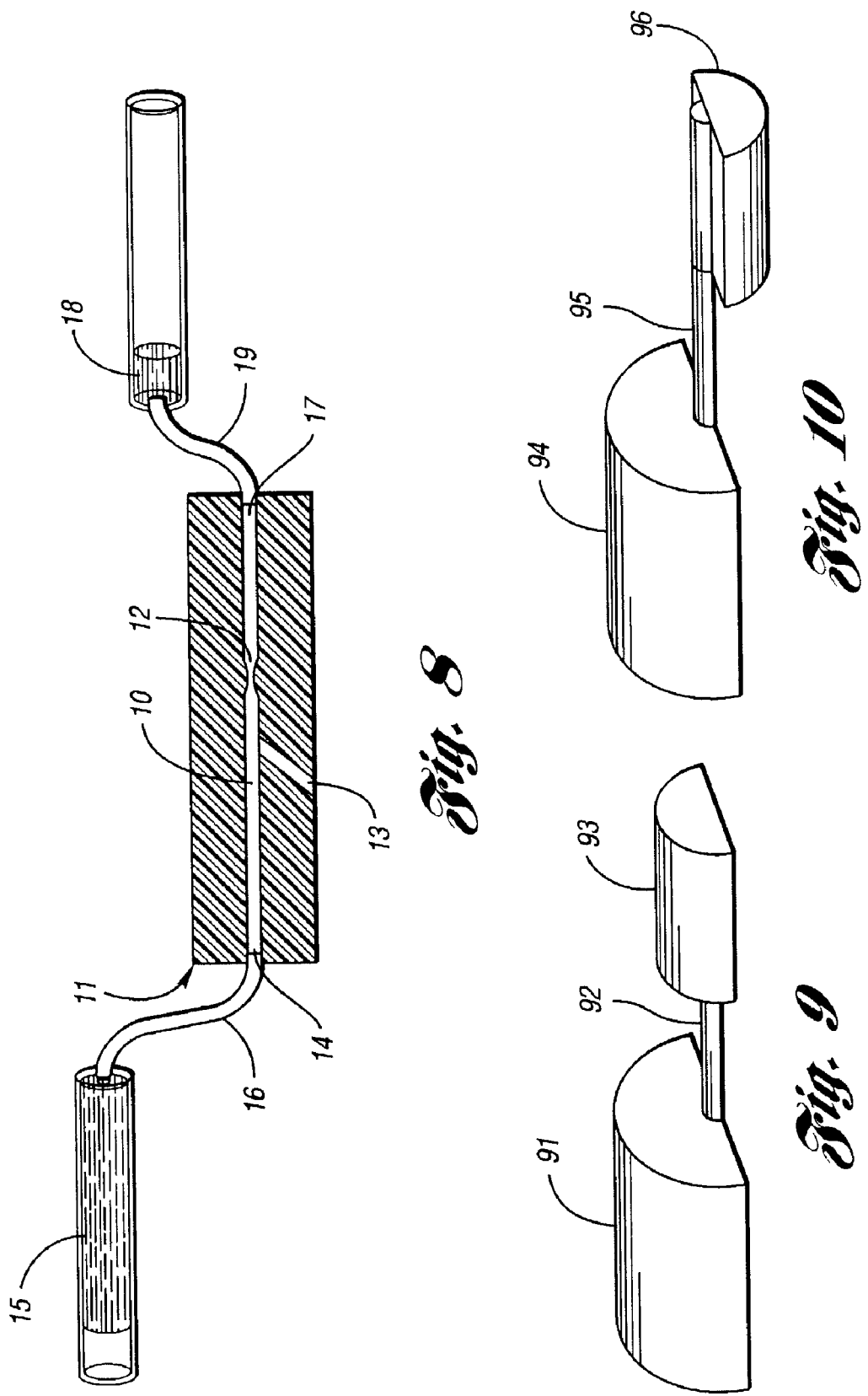

MICROFLUIDIC GRAVITY PUMP WITH CONSTANT FLOW RATE

CROSS-REFERENCE TO RELATED APPLICATION

This application claims the benefit of U.S. provisional application Ser. No. 60/306,292, filed Jul. 18, 2001.

BACKGROUND OF THE INVENTION

1. Field of the Invention

The present invention pertains to gravity driven pumps for microfluidic applications, and to microfluidic devices employing such pumps.

2. Background Art

Microfluidic devices are steadily supplanting their macroscale counterparts in numerous applications, particularly in biological and pharmaceutical research. Such devices often require one or more pumps to propel fluid through microchannels. Current methods may employ mechanical pumps such as syringe-type pumps and micromechanical pumps, and non-mechanical pumps such as electrohydrodynamic pumps, electro-osmotic flow pumps, electrowetting pumps, and thermocapillary pumps.

All these pumping systems have drawbacks associated with them. For example, a steady flow rate is difficult to achieve. Moreover, mechanical pumps require an electrical power source, as do pumps which operate based on electrical properties. Most of these pumps are costly and inconvenient to integrate with other microscale devices, and often have slow response times. Electro-osmotic flow pumps have a flow profile which is pH dependent, and which produce stable flow only over a limited pH range. Recently, a thermocapillary pump has been developed. However, this pump requires complex electronic control circuitry and creates heat transfer issues.

The use of gravity-driven flow in microfluidic applications has been attempted. However, conventional reservoirs produce a decrease in hydrostatic pressure as the liquid level in the reservoir drops. This decreasing pressure difference leads to decreased flow rates with respect to time.

It would be desirable to provide a microfluidic system including a microfluidic pump which is simple, economical to produce, and preferably disposable, which can provide a relatively constant and optionally adjustable flow rate, without the necessity for an external power source.

SUMMARY OF THE INVENTION

It has now been surprisingly discovered that a gravity driven microfluidic pump comprising a substantially horizontal supply reservoir can provide a substantially consistent flow rate in microfluidic devices which does not change as the pumped volume increases over time. The pump system of the present invention has numerous applications in microfluidic devices, including applications in in vitro testing of pharmaceutical products in environments which mimic those in vivo, in cell and embryo culture, cell sorting and other applications.

BRIEF DESCRIPTION OF THE DRAWINGS

FIG. 8 illustrates a microfluidic device useable with the subject invention gravity driven pump to monitor embryo development.

FIG. 9 illustrates one embodiment of an integrated gravity driven pump, microchannel, and outlet reservoir; and FIG. 10 illustrates a further embodiment of an integrated gravity driven pump, microchannel, and outlet reservoir.

DETAILED DESCRIPTION OF THE PREFERRED EMBODIMENT(S)

The subject invention gravity driven microfluidic pump system comprises a substantially horizontally-oriented fluid reservoir connectable to or connected to a microfluidics device having at least one microchannel through which supply liquid flows. In preferred devices, a horizontally oriented outlet reservoir receives fluid from the microchannel(s).

The fluid supply reservoir is substantially horizontal, and is of sufficient size to carry the desired amount of fluid for sustained operation. By the term "substantially horizontal" is meant a horizontal or nearly horizontal position such that the hydrostatic pressure asserted by the liquid in the supply reservoir is relatively constant. A horizontal reservoir may deviate from the absolute horizontal orientation to generate a pumping system where the hydrostatic pressure is intentionally caused to vary over time. In general, an orientation which deviates from horizontal by about 10° or less, preferably 5° or less is suitable. A very slight incline toward the outlet of the supply, i.e. 1-3°, may be useful to counter effects due to surface tension between the liquid being pumped and the walls of the reservoir. Moreover, in actual pump configurations in the laboratory, it may be difficult to adjust the orientation of the device to a purely horizontal configuration.

Due to the volume generally required to supply fluid over time, the volume of the supply reservoir is normally considerably greater than the volume of the microchannel(s) through which fluid flow is desired. For example, at flow rates of 1000-3000 nL/hr, the reservoir may be several mL in volume. The reservoir volume is generally at least 10 times the volume of the microchannel(s), preferably more than 100 times the volume of the channel. The reservoir preferably has an aspect ratio (length:inside diameter) of at least 5:1, preferably at least 10:1, and more preferably at least 100:1.

Figure 1:
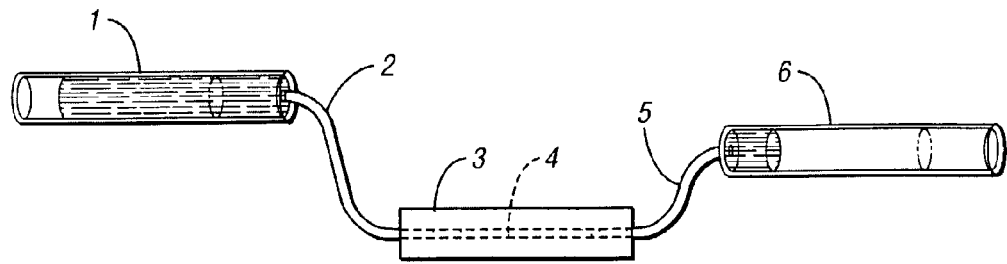
FIG. 1 illustrates schematically one embodiment of a microfluidic device employing a gravity driven pump of the present invention.

The reservoir may constitute a straight run of hollow tubing, for example of glass, and may also be bent in a U-configuration or in a horizontal spiral to conserve space. A suitable configuration is shown in FIG. 1, wherein fluid in supply reservoir 1 flows through tubing 2 to microfluidics device 3, in this case having a single microchannel 4. From microchannel 4, fluid flows through tubing 5 to outlet reservoir 6, the "shadowed" ellipses indicating the positions of the menisci in the supply and outlet reservoirs after a period of flow has occurred. The internal cross-section of the hollow tubing may be of any desired shape. Preferably, the internal cross-section is round, but elliptical, square, rectangular, octagonal, ("polyhedral") or other cross-sections may be used as well. The cross-sectional shape of the reservoir may be of any shape (circle, square, rectangle, etc) as long as the shape is such that it maintains enough surface tension to keep the fluid inside from spilling out. The cross-sectional shape may vary along the length of the reservoir to program different hydrostatic pressures at different points in time determined by the amount of fluid volumes present in the reservoirs. The supply reservoir may be a separate device connected permanently to, or connectable to, the microfluidic device, or may be integrated into the device. For example, a glass tubing reservoir may have standard microfluidics connectors which enable connection to a microfluidic device channel through suitable tubing, for example hollow tubing of polydimethylsiloxane elastomer ("PDMS"), polysulfone, etc. Alternatively, a PDMS or other polymer device may be fabricated to contain both the supply reservoir and the microchannel through which flow is desired as shown in but two embodiments in FIGS. 9 and 10. In such devices, at least a portion of the supply reservoir and the microchannel(s) are at different heights, so that when positioned such that the supply reservoir is horizontal, a gravity-created hydrostatic pressure condition exists between the reservoir and the microchannel outlet. The microchannel may be horizontal, inclined or vertical, preferably horizontal.

The diameter of the fluid supply reservoir is only critical to the extent that the surface tension between the fluid and the walls of the reservoir is sufficient to maintain the liquid within the reservoir at a given reservoir internal diameter, and the internal diameter is not so small as to prevent fluid flow due to the surface tension. This relationship between surface tension and internal diameter will vary depending upon several factors, including the geometry of the internal cross-section of the reservoir, the nature of the inner walls of the reservoir, and the nature of the fluid. The suitability of any particular reservoir may be assessed easily by filling the reservoir with liquid and observing whether the reservoir will hold the liquid stably through the microchannel when connected thereto.

For example, reservoirs of square or rectangular cross-section will be expected to allow for larger "diameters" than those of circular cross-section due to increased interaction between the fluid and the walls at the corners of the internal cross-section and the higher surface to volume ratio of non-circular cross-sections. For aqueous fluids, internal walls which are hydrophilic will exhibit lesser fluid/wall interactions than surfaces which are less hydrophilic (or more hydrophobic). Finally, the nature of the fluid itself is important. The presence of surface tension-lowering compounds in the fluid will alter the maximum "diameter" accordingly.

For example, with a fluid which contains 1.0 weight percent BSA (bovine serum albumin), glass tubing of diameters from 2.5 mm to 6.0 mm were tested. It was found that with this fluid, 5-6 mm inside diameter ("I.D.") tubing was incapable of holding fluid by surface tension, whereas tubing of 2.5 mm exerted too high a surface tension, preventing fluid flow or minimizing fluid flow to such an extent that the pump is essentially inoperable. However, tubing with nominal diameters between 3.5 mm and 4.0 mm were found to be eminently well suited as a reservoir for such applications. The suitability for any given internal "diameter"/configuration can be simply assessed by ascertaining, first, whether fluid can be held within the reservoir by orienting the reservoir horizontally and determining that the fluid will not flow out of its own accord; and second, by ascertaining that the interaction between the wall of the reservoir and the fluid is not so high that the desired flow rate between the reservoir and a given microchannel cannot be obtained.

The microfluidic device contains at least one microchannel through which fluid flows due to hydrostatic pressure exerted by a difference in height (relative to gravitational field) between the supply reservoir and the microchannel. The microfluidic device may contain but a single microchannel, may contain a plurality of converging microchannels, may contain a plurality of parallel microchannels, or any combination thereof. The microchannels must be of sufficient size such that flow of fluid is possible. In other words, the internal diameter of the microchannels must not be so small that the devices "lock up" once fluid full, whereby fluid flow is prevented. In general, the diameter of the microchannels, if circular, is from 1 μm to about 5 mm, preferably 10 μm to about 3 mm, more preferably 100 μm to 2 mm. As with the supply reservoirs, the internal size is related to the channel cross-section, hydrophilicity/hydrophobicity, and fluid nature.

The microchannels of the device are terminated in an outlet. The outlet is preferably in fluid communication with a fluid reservoir, in order to prevent fluctuations in pressure associated with formation of "drops" from the outlet. The outlet reservoir may be a simple container with which the microchannel communicates, or preferably is an outlet reservoir of the same size, material, and geometry as the supply reservoir. In such a situation, capillary forces cancel out and hydrostatic pressure due to gravity is the only driving force for the liquid.

When the supply reservoir and outlet reservoir are of the same configuration and construction, the effects of geometry-induced and constitution-induced (i.e. hydrophilic/hydrophobic) properties may be completely offset, thus increasing the constancy of flow. For example, when the supply reservoir consists of a 4 mm I.D. pyrex glass tube, the outlet reservoir may also consist of a 4 mm I.D. pyrex glass tube as well. In such cases, once the device is initially filled with fluid, i.e. by application of a slight pressure differential between the supply reservoir and the outlet, fluid flow may occur from reservoirs whose internal size is too small for flow without the use of a similar outlet reservoir.

The effects of surface tension in the supply and outlet reservoirs may be changed by rendering these surfaces increasingly hydrophilic or hydrophobic, or by surface treatments which are specific to fluid components. For example, glass surfaces may be rendered more hydrophobic by reaction of the surfaces with hydrophobicizing compounds such as octyltrimethoxysilane and perfluoropropyltriethanoxysilane and like compounds. Such silanes react with silanol groups on the silica surface. If a glass surface is desired to be rendered more hydrophilic, it may similarly be reacted with silanes which bear hydrophilic groups, i.e. polyoxyethylene/polyoxypropylene groups or glycosidyl groups. For other than silica-based reservoirs, for example of organic polymers, numerous reagents are known which effect hydrophilization/hydrophobicization. Use of perfluoroalkyl compounds allows alteration of surface tension both with respect to water (aqueous compositions) as well as oleaginous compositions (i.e. paraffinic solvents). A net capillary force may also be generated by the reservoirs by adjusting the cross-sectional areas of the reservoirs. In these cases there would be a combination of gravitational and capillary force that would pump the fluid.

The fluid flow of gravity driven pumps of the subject invention is easily adjusted. For example, positioning the height of the supply reservoir at increasing heights above the outlet reservoir can be used to increase fluid flow appropriately. If fluid flow is desired to be altered during operation of the device, a robotic device may be manually or programmably directed to increase or decrease the relative height differences between the inlet and outlet. Thus, the flow rate can be increased or decreased in any manner, i.e. linearly, sinusoidally, stepwise, etc.

Programmed flow rates may also be provided without resort to robotic devices or the like by altering the nature of the walls of the supply or outlet reservoirs at specific locations, or their internal size. For example, in a cylindrical supply reservoir such as a length of glass tubing, a first portion of the internal walls of the tubing may be rendered hydrophobic while a second portion may be hydrophilic. The rate of flow will alter in a stepwise manner when the liquid in the tube reaches the boundary between the hydrophobic and hydrophilic surfaces due to a change in surface tension at this point. Alternatively, an inlet reservoir may be configured to have succeeding portions stepped in height, for example a portion most remote from the microchannel(s) to which fluid is supplied having a height higher than a closer portion. The flow will be constant from the first (higher) portion of the reservoir, and then fall in a step fashion as the fluid level in the higher reservoir falls to the level in the lower reservoir, when flow will again remain constant, but at a lower rate.

The channels of the microfluidic devices may be treated to encourage adhesion of a variety of substrates whose interaction with the supply fluid and/or its components is desired. The treatment of the microchannels may take place prior to assembly of a complete microfluidics device, or may take place after assembly. In preferred devices, treatment of the microchannel surfaces takes place prior to assembly of the device.

The microfluidic devices used in accordance with the subject invention may be any microfluidic device, particularly microfluidic devices for which a relatively constant fluid flow is desired. Numerous uses are possible, including motile sperm sorters, B. Cho, et al. Proceedings of the IEEE-EMBS Conference on Microtechnologies in Medicine and Biology, pp. 156-159 (2002), and cell size sorting, D. Huh, et al., Proceedings of the 2nd IEEG-EMBS Conference, pp. 466-469 (2002), incorporated herein by reference.

For example, in the in vitro testing of pharmacologically active compounds, it is recognized that a difference in observed in vitro activity is observed as opposed to in vivo activity. This discrepancy is believed by some to be the result of exposure of cells and cell components to presence of fluid flow in vivo whereas most assessments of activity in vitro are assessed under static conditions. For example, mechanical extracellular forces, in particular on endothelical cells and smooth muscle cells, have been studied extensively. Laminar sheer stress within blood vessels cause endothelial cells to express factors which inhibit platelet coagulation, leukocyte adhesion and migration, LDL accumulation, and endothelial cell maintenance. Mass transport also changes with fluid flow. Delivery of oxygen, nutrients and removal of waste materials and autocrine factors are also affected by fluid flow. An effective tool to monitor these flow-related phenomena under steady flow rather than under static conditions is needed; the present invention supplies the ability to do so in a cost-effective and efficient manner.

Thus, the present invention further pertains to a method of observing and/or analyzing flow related sheer stress-related phenomena in biological systems where the analysis requires or prefers a steady flow of fluid as is provided by the gravity driven microfluidics pumps of the present invention.

Within microfluidic culture environments for human and non-human embryos, a dynamic culture system holds numerous advantages in comparison to current static culture systems. First, gradual movement of media over embryos would have the ability to remove metabolic by-products such as ammonia and oxygen free radicals which are detrimental to embryo development. In addition, individual blastomeres (cells) that comprise the embryo can undergo apoptotic death, fragmentation and release of apoptotic cell death agents that may be detrimental to survival of remaining blastomeres. A dynamic culture system would remove such agents. Second, current human embryo culture strategies use 2-3 sequential media for 3-6 day culture with abrupt media changes, which can inflict osmotic stress upon embryos. A dynamic culture system would allow gradual media changes that may be beneficial. Third, within the oviduct, cilia of epithelial cells are continuously "beating" causing constant movement of pre-implantation embryo(s). Such movement, which can be achieved with dynamic media flow, may be beneficial for establishing poles-of-cell division and enhance embryo developmental competence. Fourth, dynamic media flow over embryos will allow "sampling" of embryo by-products that have potential of indicating which embryos have the greatest change of implantation and pregnancy establishment. Lastly, group embryo culture is believed to be superior to individual culture based on the idea that more developmentally advanced embryos ("helpers") produce substances that enhance poorer embryo ("lagger") development. Conversely, poorer developing embryos may have detrimental influence on more advanced embryos. Culture devices using dynamic media flow may facilitate "helper" embryo influences on "lagger" embryo development without negative reciprocal effects. For the effects of fluid flow on embryo development, reference may be had to S. Nonaka et al., "Determination of Left-Right Patterning of the Mouse Embryo by Artificial Nodal Flow," NATURE, 418, pp. 96-99, July, 2002.

A device suitable for studying embryo development is illustrated in FIG. 8. In FIG. 8, the microchannel 10 has a portion 12 which is constricted in at least one dimension or bears a grid, post, or other structure capable of holding an embryo in place under flow conditions. The embryo may be introduced into the microchannel by numerous means, as shown in FIG. 8 by a converging channel 13 which is sealed off once the embryo is in place. Other means which restrict the clear path, such as a grid, post, protuberance, etc., are also acceptable, so long as flow around the embryo can be maintained. The upstream end 14 of the microchannel is connected to horizontal supply reservoir 15 by tubing or passageway 16 which the downstream end 17 is an outlet, preferably connected to outlet reservoir 18 by tubing or passageway 19.

The rate of flow produced by the pumps of the present invention is adjusted by altering the height of the supply reservoir above the microfluidics device. For example, heights from 0.1 mm to about 4 m are suitable, more preferably from 1 mm to 1 m, yet more preferably from 10 mm to 750 mm, and most preferably in the range of 10 mm to 100 mm. Devices with low flow rates and concomitantly low supply reservoir heights are suitable for single device fabrication.

Among preferred embodiments of the subject invention, microfluidic devices are those wherein a supply reservoir and an outlet reservoir are constructed integrally with the microfluidic channel(s), and those wherein the device is constructed such that the microchannel can temporarily retain an open side onto which cells can be plated prior to sealing off the microchannel.

In the first of these preferred embodiments, supply and reservoir channels may be fabricated on the same substrate as the microchannel itself. Such devices then need only to be supplied with the appropriate fluid(s) to function. The reservoirs and microchannels of two such devices are shown in FIGS. 9 and 10. In both these devices, the supply reservoir is considerably greater in volume than the microchannel volume so that flow may occur for some length of time. In FIG. 9, the supply reservoir 91 is somewhat larger in area and taller than the outlet reservoir 93. When filled with fluid, the height difference of the two reservoirs allows fluid flow through microchannel 92 until the heights of fluid in the two reservoirs is equal. In FIG. 10, the outlet reservoir 96 is configured lower than the supply reservoir 94 in its entirety, allowing complete emptying of the supply reservoir through microchannel 95 providing the volume of the outlet reservoir is sufficient to accept the required fluid volume.

In the second of the above embodiments, the device may be cast, for example of PDMS, and upon removal from the mold, the microchannel and reservoirs, when present, will be open on the side facing the mold. These surfaces can be appropriately plated with cells, or treated with substances which promote or inhibit cell adhesion. The various channels and/or reservoirs may also be closed temporarily to facilitate single or multiple coating/plating processes. For example, portions of the device, for example, the channel may be coated with cell adhesive proteins in the closed channel state, and other surfaces coated with non-cell adhesive protein. The device may be peeled of its temporary "closing" backing, and then, in the open state, cells may be plated. Plating cells in the open state, before making the closed channel system, while achieving selective cell attachment inside the channel, is important for allowing rapid plating of cells into the channels. After cells attach, the channel system is closed again.

Having generally described this invention, a further understanding can be obtained by reference to certain specific examples which are provided herein for purposes of illustration only and are not intended to be limiting unless otherwise specified.

Example 1

A microfluidic device is constructed from PDMS by micromachining a silicon substrate and casting a curable PDMS onto the substrate to obtain a PDMS slab with embedded channel features. Reference may be had to S. Takayama, et al. "Patterning Cells and Their Environment Using Multiple Laminar Fluid Flows in Capillary Networks," PROC. NATL. ACAD. SCI. USA, pp. 5545-48, 1999; Duffy et al. "Rapid Prototyping of Microfluidic Systems in Poly(dimethylsiloxane), ANAL. CHEM. 70, pp. 4974-84, 1998. The microchannel is ca. 4 mm in width. The channel is sealed by conformal contact with a planar PDMS slab.

A 5/32" (4 mm) inside diameter glass tube is employed as the supply reservoir and is positioned horizontally on a stand with one end open and the other (supply) end connected with a 0.030 (0.75 mm) I.D., 0.065 O.D. (1.65 mm) silicone tubing (VWR Scientific). The silicon tubing is sealed to the inlet of the microchannel of the PDMS microfluidic device with epoxy resin. The outlet of the microchannel is similarly sealed to another piece of silicone tubing, which is connected to a glass tube (outlet reservoir) of the same diameter as the supply reservoir.

Figure 2:
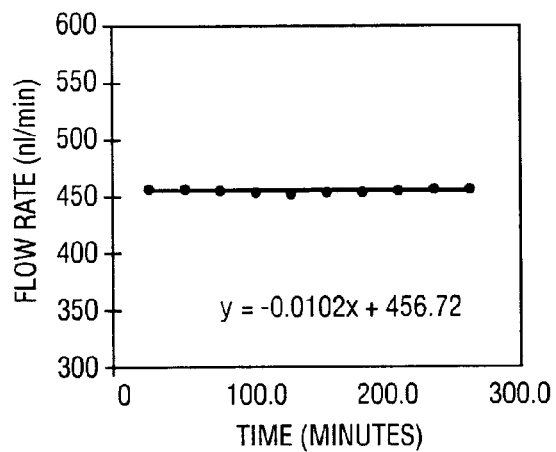
FIG. 2 illustrates flow rate against time of an embodiment of Example 1 of the present invention.

To initially fill the channel system with liquid, the liquid-filled reservoir is held high and optionally tilted to allow rapid loading of the microchannel. The supply reservoir is then situated approximately horizontally at a level similar to that of the outlet glass reservoir, the latter serving as the fluid outlet reservoir. The supply reservoir is then raised above the level of the outlet reservoir, and the meniscus at the front of the pumped liquid monitored using a horizontally oriented stereoscope (Nikon SMZ-1500). Time lapsed images are captured with a CCD camera (Hamamatsu Orca-100) to monitor the flow meniscus in the horizontally positioned flow supply reservoir at 60 sec. intervals. Resolution between adjacent images is about 80 pixels. The flow rate is plotted against time and found to be substantially constant, as indicated by FIG. 2, a plot of flow rate in nL/min versus time, with a slope of $y=-0.0102x+456.72$. Less than a 1% variation in flow rate is demonstrated, within the limitation of the resolution of the CCD (80 pixels/meniscus front=1.25%).

Figure 3:
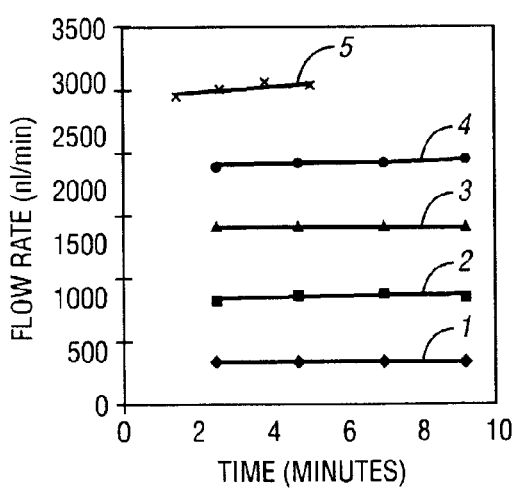
FIG. 3 illustrates flow rates at various heights of the device of Example 1.
Figure 4:
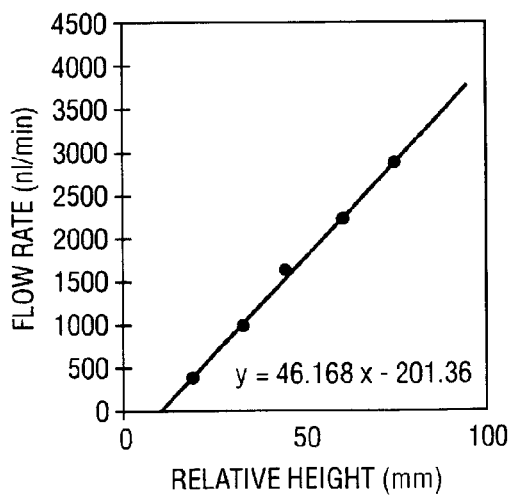
FIG. 4 illustrates the linear relationship between height and flow rate of the device of Example 1.

The flow rate at various supply reservoir heights relative to the outlet reservoir is assessed similarly. A plot of flow rates is shown in FIG. 3, where 1 represents a height of 19.5 mm, 2 a height of 33.3 mm, 3 a height of 44.7 mm, 4 a height of 50.3 mm and 5 a height of 75.5 mm. The relationship between supply reservoir height and flow rates is substantially linear, as shown in FIG. 4.

Example 2

Figure 5:
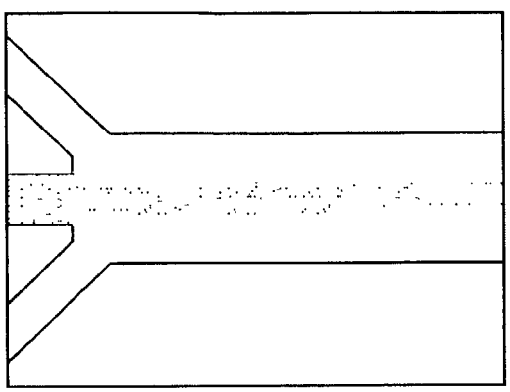
FIG. 5 illustrates a microfluidic device having converging inlets and the flow produced therein in accordance with Example 2.

In the same manner as Example 1, a multiple-inlet microfluidics device is fabricated from PDMS, having a central inlet and two flanking inlets. The central inlet is connected to a substantially horizontal fluid reservoir of water containing a red dye, whereas the flanking inlets are connected to a water reservoir. The flow is illustrated by FIG. 5. The widths and shape of the flow remained unchanged for 36 hours. The microchannel width is about 300 µm, and each of the supply channels is about 100 µm.

Example 3

Figure 6:
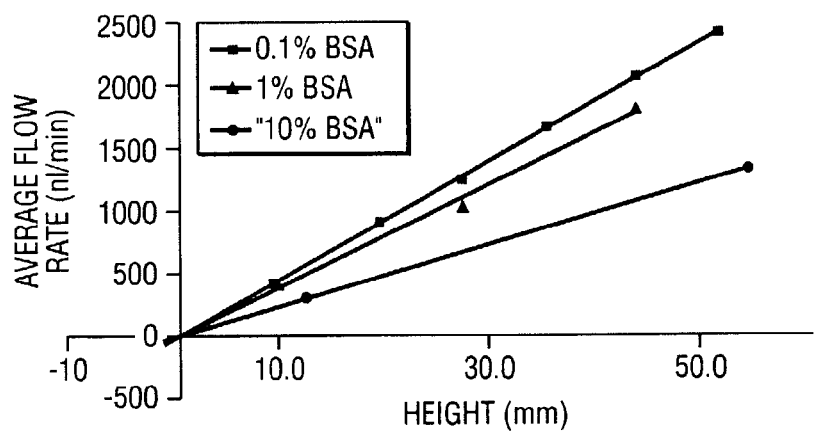
FIG. 6 illustrates the effect of concentration of BSA an flow rates in the device of Example 1.

The effect of different fluids on the flow rate is shown by FIG. 6, wherein the flow rate at various heights are monitored with three different concentrations of BSA: 0.1% by weight, 1% by weight, and 10% by weight. As expected, the flow rate declines with increasing BSA concentration.

Example 4

Figure 7:
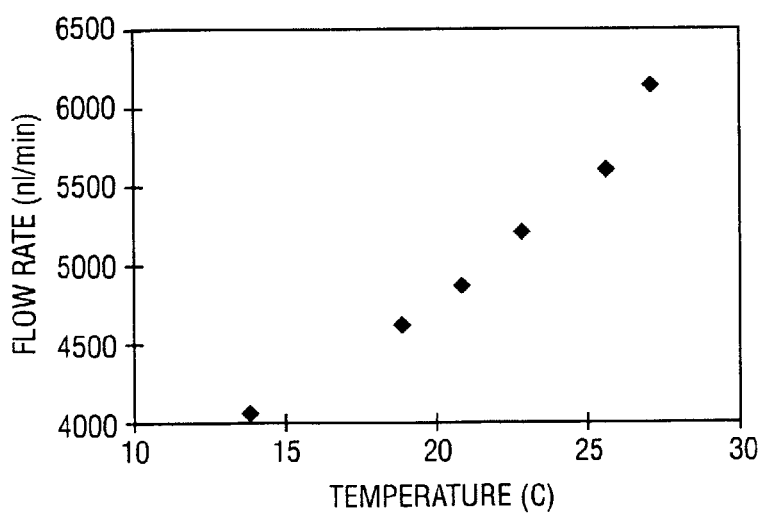
FIG. 7 illustrates the effect of temperature on flow rate in accordance with Example 4.

The flow rate of 1% BSA is monitored at different temperatures. A plot of the temperature dependence is shown in FIG. 7, the flow rate increasing from about 4000 nL/min. at ca. 14° C. to ca. 6300 nL/min at ca. 27° C.

Example 5

The use of the present devices employing constant flow pumps for cell plating/culture is demonstrated by plating c2c12 cells onto select regions of a microfluidic device. It has proven difficult to provide high cell density in completely closed devices; hence, cell plating is accomplished prior to "closing" of the microchannel.

A negative substrate is produced onto which PDMS is cast, providing a 3 cm long microchannel having a height of 40 µlm and width of 1 mm, an inlet reservoir 3 mm in height and 4 mm in width, and an outlet reservoir of 2 mm height and 4 mm width on either side of the microchannel.

The PDMS layer is removed from the "master," and the channel, along with a trough (to be filled with media and cells) are sterilized under UV light for 20 minutes, following which the PDMS slab with channel is placed on a glass slide with the channels facing the glass slide. The inlet reservoir is filled with 2% BSA solution, and incubated at room temperature for 30 mins. The BSA solution does not enter the microchannel due to its hydrophobicity and lack of hydrostatic pressure at the inlet reservoir. The BSA solution is sucked out of the inlet reservoir by a pipet resulting in a BSA coated inlet reservoir. The channel and outlet are not coated.

A cell adhesive protein, such as collagen DQ, is introduced into the outlet reservoir and forced into the channel, following which the device is incubated at room temperature for 45 minutes. BSA solution (2%) is again introduced into the inlet reservoir, and forced into the channel employing pressure at the inlet or suction at the outlet to rinse remaining collagen from the channel. The outlet reservoir is rinsed with 2% BSA solution as well.

The PDMS layer is peeled off the glass slide and covered with 2% BSA, followed by incubation at room temperature for 30 min. The BSA solution is rinsed off the device using sterile Phosphate Buffered Saline ("PBS"), and the PDMS layer is stored in a BSA-containing Petri dish (to prevent drying out). The PDMS channel is then placed in a petri dish with channel opening facing up and exposed, and the device covered with media, consisting of Dulbecco's Modified Eagle Medium ("DMEM") plus 10% fetal bovine serum ("FBS") plus 1% Penicillin G.

A culture dish with cells was evaluated to ensure that living c2c12 cells are present, and the media is removed. Cells were rinsed with 4 mL sterile PBS, following which 0.5 mL trypsin was added to the culture dish and incubated at 37° C. for 2 min. 2 mL of media was then added to the culture dish to wash off cells, following which the cells were collected, centrifuged, and a portion of the supernatant removed. The cells were plated onto the PDMS channels (channel side facing up and exposed to medium) and they were incubated in the channel in a 37° C. incubator and viewed microscopically for attachment at 12 hour intervals for 72 hours. Unattached cells were removed by rinsing with sterile PBS. Cells attached preferentially to regions inside the channel because that is the only region coated with cell adhesive protein. Other regions were coated with BSA.

The cell-plated PDMS channels were then placed against a flat surface, channel side down, to provide a closed channel system with cells attached to the PDMS channel walls. The inlet reservoir itself can serve as the gravity pump reservoir or may also be attached to a horizontal fluid supply reservoir containing cell culture media. Culture of c2c12 cells under continuous, substantially constant flow is exhibited.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A gravity driven pump comprising:
   at least one microchannel with an inlet in fluid communication with a first horizontally oriented fluid supply reservoir and an outlet in fluid communication with a second horizontally oriented fluid supply reservoir, wherein the ceiling of the first supply reservoir is positioned above the ceiling of the second supply reservoir;
   wherein the first fluid supply reservoir comprises a plurality of sections having different heights, hydrophilicities, or hydrophobicities, such that liquid within each section of the supply reservoir (i) occupies the entire internal height of the first supply reservoir as liquid flows out of the supply reservoir and (ii) flows at a generally constant rate within each section, such that rate of flow will alter in a stepwise manner, without moving the supply reservoirs, based on the heights, hydrophilicities, or hydrophobicities of each section of the first fluid supply reservoir.

2. The gravity driven pump of claim 1, wherein the first supply reservoir comprises a hollow length of tubing having an internal volume minimally 100 times the internal volume of the at least one microchannel.

3. The gravity driven pump of claim 2, wherein the first supply reservoir has a circular, elliptical, or polyhedral internal cross-section.

4. The gravity driven pump of claim 2, wherein the tubing is configured in a series of generally U-shaped bends or as a horizontal spiral.

5. The gravity driven pump of claim 1, wherein the first supply reservoir has an aspect ratio of at least 5:1.

6. The gravity driven pump of claim 1, wherein the supply reservoir has an internal dimension d and wherein the second fluid supply reservoir has an internal dimension d' such that capillary forces exerted between liquid in the first supply reservoir and the first supply reservoir are substantially the same as capillary forces exerted between liquid in the second supply reservoir and the second supply reservoir.

7. The gravity driven pump of claim 1, wherein the rate of flow for each section is constant within +1% of volume flow when the height of the first supply reservoir above the outlet is fixed.

8. The gravity driven pump of claim 1, wherein the height of the first supply reservoir above the outlet is alterable.

9. The gravity driven pump of claim 1, further comprising a single microchannel in fluid communication with minimally two horizontally oriented liquid supply reservoirs.

10. The gravity driven pump of claim 1, further comprising a plurality of microchannels in fluid communication with at least one horizontally oriented supply reservoir.

11. The gravity driven pump of claim 10, wherein a plurality of microchannels are in fluid communication with one supply reservoir.

12. The gravity driven pump of claim 1, wherein the first supply reservoir and the at least one microchannel are constructed of a polymer.

13. The gravity driven pump of claim 12, wherein the polymer comprises an organopolysiloxane polymer.

14. The gravity driven pump of claim 1, wherein the at least one microchannel retains an open side onto which cells can be plated before producing a closed microchannel system.

15. The gravity driven pump of claim 10, wherein selected portions of internal passages of the gravity driven pump are treated with cell adhesive proteins and other selected portions are treated with a non-cell adhesive protein.

16. The gravity driven pump of claim 1, the gravity driven pump having a body portion, an inlet reservoir within the body portion in direct fluid communication with an upstream end of at least one microchannel, a secondary outlet reservoir in direct fluid communication with a downstream end of at least one microchannel, the inlet reservoir fluidly communicatable with a horizontally oriented liquid supply reservoir.

17. The gravity driven pump of claim 1, further comprising a structure in communication with the at least one microchannel, the structure sized such that the structure prevents passage of an embryo to the outlet, but which allows for fluid flow around the embryo.

18. The gravity driven pump of claim 17, wherein the structure comprises a narrowing of the at least one microchannel in at least one dimension.

19. The gravity driven pump of claim 17, wherein the structure comprises a protuberance into the at least one microchannel from a wall of the at least one microchannel.

20. The gravity driven pump of claim 17, wherein the structure comprises a grid or post.

21. The gravity driven pump of claim 1 wherein liquid in the first supply reservoir forms a substantially vertical meniscus as the liquid is removed from the first supply reservoir.

* * * * *

UNITED STATES PATENT AND TRADEMARK OFFICE
CERTIFICATE OF CORRECTION

| | |
|---|---|
| PATENT NO. | : 7,704,728 B2 |
| APPLICATION NO. | : 10/198477 |
| DATED | : April 27, 2010 |
| INVENTOR(S) | : Shuichi Takayama et al. |

It is certified that error appears in the above-identified patent and that said Letters Patent is hereby corrected as shown below:

Column 10, Line 9, Claim 6:

After "wherein the" and before "supply" insert -- first --.

Column 10, Line 17, Claim 7:

After "within" delete "+1%" and insert -- ±1% --.

Signed and Sealed this

Twenty-ninth Day of June, 2010

David J. Kappos
*Director of the United States Patent and Trademark Office*